(12) United States Patent
Su et al.

(10) Patent No.: US 7,214,490 B2
(45) Date of Patent: May 8, 2007

(54) METHOD OF TARGET ENRICHMENT AND AMPLIFICATION

(75) Inventors: Xing Su, Cupertino, CA (US); Shoulian Dong, San Jose, CA (US)

(73) Assignee: Affymetrix, Inc., Santa Clara, CA (US)

(*) Notice: Subject to any disclaimer, the term of this patent is extended or adjusted under 35 U.S.C. 154(b) by 511 days.

(21) Appl. No.: 10/654,281

(22) Filed: Sep. 2, 2003

(65) Prior Publication Data

US 2004/0132056 A1    Jul. 8, 2004

Related U.S. Application Data

(62) Division of application No. 09/910,292, filed on Jul. 19, 2001, now Pat. No. 6,632,611.

(51) Int. Cl.
*C12Q 1/68* (2006.01)
*C12P 19/34* (2006.01)
*C07H 21/04* (2006.01)

(52) U.S. Cl. .............. 435/6; 435/91.2; 435/91.1; 435/91.51; 435/91.52; 536/24.3; 536/24.2

(58) Field of Classification Search .............. 435/6, 435/91.2, 91.52, 91.51; 536/24.3, 24.2
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,501,964 A | 3/1996 | Wigler et al. | |
| 5,712,127 A | 1/1998 | Malek et al. | |
| 5,763,239 A | 6/1998 | Short et al. | |
| 5,858,656 A | 1/1999 | Deugau et al. | |
| 5,876,929 A | 3/1999 | Wigler et al. | |
| 6,001,574 A | 12/1999 | Short et al. | |
| 6,060,245 A | 5/2000 | Sorge et al. | |
| 6,063,623 A * | 5/2000 | Koepsell et al. | 435/371 |
| 6,287,825 B1 | 9/2001 | Weissman et al. | |
| 6,455,255 B1 | 9/2002 | Birkenmeyer et al. | |
| 2003/0082530 A1* | 5/2003 | Soderlund et al. | 435/6 |

FOREIGN PATENT DOCUMENTS

| | | |
|---|---|---|
| WO | WO 00/18960 | 4/2000 |
| WO | WO 01/75163 A2 | 3/2002 |
| WO | WO 02/20844 A1 | 3/2002 |

OTHER PUBLICATIONS

Nikolai Lisitsyn, et al., "Cloning the Differences Between Two Complex Genomes", Research Article, Science, vol. 259, Feb. 12, 1993, pp. 946-951.

* cited by examiner

*Primary Examiner*—Kenneth R. Horlick
*Assistant Examiner*—Joyce Tung
(74) *Attorney, Agent, or Firm*—Sandra E. Wells

(57) ABSTRACT

The presently claimed invention provides methods and kits for amplifying a target sequence from within a nucleic acid population. The presently claimed invention provides selection probes which are complementary to at least a portion of said target sequence and mechanisms for adding a probe sequence to the 3' end of a target sequence that is hybridized to a selection probe. The added 3' probe sequence and a probe sequence added at the 5' end of the target by adaptor ligation allow for selective amplification of the target sequence.

16 Claims, 6 Drawing Sheets

| Selection probe RNA \ Sample DNA | 10k copies of genome + 20x each Positive control 1 + 20x each Positive control 2 | 10k copies of genome + 1x of each Positive control1 + 1x of each Positive control 2 |
|---|---|---|
| Positive control 1 each 1x10¹⁰ copies | A | B |
| Positive control 2 each 1x10¹⁰ copies | C | D |

Fig. 3B

METHOD OF TARGET ENRICHMENT AND AMPLIFICATION

RELATED APPLICATIONS

This is a divisional application of U.S. application Ser. No. 09/910,292, filed Jul. 20, 2001 now U.S. Pat. No. 6,632,611.

FIELD OF INVENTION

The present invention is in the field of nucleic acid hybridization. More specifically, the present invention is in the field of nucleic acid hybridization and enrichment.

BACKGROUND OF THE INVENTION

Methods of amplifying target DNA sequences can be costly and complicated, often requiring large numbers of specific primer sequences that must be synthesized for each experiment. One aspect of the present invention provides a process that is cost effective and straight forward for enriching and amplifying specific nucleic acid sequences including polymorphic regions, chromosomal regions and whole chromosomes.

SUMMARY OF INVENTION

The currently claimed invention provides novel methods for the enrichment and amplification of target sequences from a nucleic acid population using selection probes. The invention further provides for analysis of the sample by hybridization to an array, which may be specifically designed to interrogate the desired fragments for particular characteristics, such as, for example, the presence or absence of a polymorphism.

In a first embodiment, the currently claimed invention provides a method of amplifying a population of target sequences wherein each of said target sequences comprises a region of interest. The method comprises fragmenting a sample nucleic acid population, ligating an adaptor sequence to the 5' end of the fragments and exposing the fragments to selection probes. The selection probes comprise a region that is complementary to a region of interest and a unique sequence at the 5'end. Target sequences and selection probes are allowed to hybridize forming probe-target complexes. The target sequence is then extended at the 3' end using the selection probe as a template. As a result the extended target will contain a unique sequence at its 3' end that is the complement of the unique sequence at the 5' end of the selection probe. The target can then be selectively amplified using a first primer that recognizes the unique sequence added to the 3' end and a second primer that recognizes the 5' adaptor sequence.

In another embodiment the presently claimed invention provides a method of amplifying a population of target sequences wherein each of said target sequences comprises a region of interest. The method comprises fragmenting a double stranded population, making the population single stranded by selectively degrading one strand, exposing the fragments to selection probes to form target-probe complexes, removing single stranded nucleic acids, leaving completely double stranded probe-target complexes, ligating adaptors to the ends of the probe-target complexes and amplifying the probe target complexes using primers that are complementary to the adaptors. The selection probes comprise a region that is complementary to the region of interest.

In yet another embodiment, the invention relates to a kit comprising reagents and instructions for reproducibly amplifying a population of target sequences. The kit may comprise a plurality of selection probes, reagents and instructions necessary for amplification of one or more regions of interest. The kit may also comprise a means to generate selection probes.

The present invention also provides methods for genotyping an individual which may further comprise contacting the amplified target sequences with a solid support comprising nucleic acid probes, and detecting the presence or absence of hybridization of the target sequence to the nucleic acid probes on the solid support. The immobilized probes in a preferred embodiment are capable of interrogating one or more polymorphic sites. The identity of the polymorphic base is determined from the hybridization information. In a preferred embodiment, the solid support, which may comprise nucleic acid probes, can be selected from the group consisting of a nucleic acid probe array, a membrane blot, a microwell, a bead, and a sample tube.

In another embodiment the presently claimed invention provides a method for making a population of selection probes to be used in the current invention. The selection probes are particularly useful if they are a subset of a complex population. For example a particularly useful population of selection probes would be a subset of a genome.

BRIEF DESCRIPTION OF THE DRAWINGS

FIG. 3B shows a graphical representation of the set up of the experimental samples.

DETAILED DESCRIPTION (A) General

Figure 1:
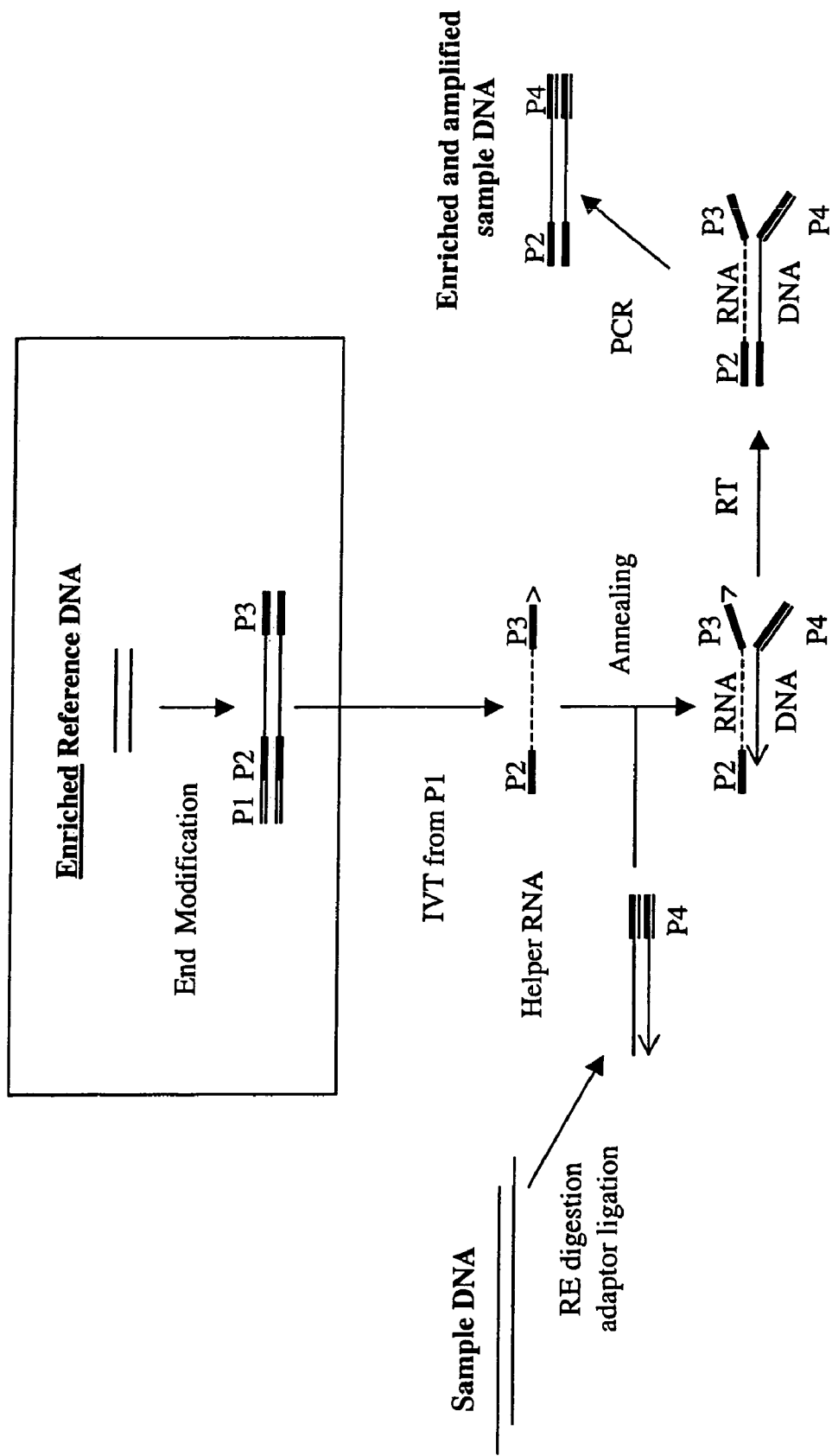
FIG. 1 is a schematic illustration of a method for amplifying a target sequence from a nucleic acid population by hybridizing selection probes to target molecules and extending the target molecule to include a primer binding site.

The present invention relies on many patents, applications and other references for details known to those of the art. Therefore, when a patent, application, or other reference is cited or repeated below, it should be understood that it is incorporated by reference in its entirety for all purposes as well as for the proposition that is recited. As used in the specification and claims, the singular form "a," "an," and "the" include plural references unless the context clearly dictates otherwise. For example, the term "an agent" includes a plurality of agents, including mixtures thereof. An individual is not limited to a human being but may also be other organisms including but not limited to mammals, plants, bacteria, or cells derived from any of the above.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as common individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. The same holds true for ranges in increments of $10^5$, $10^4$, $10^3$, $10^2$, 10, $10^{-1}$, $10^{-2}$, $10^{-3}$, $10^4$, or $10^{-5}$, for example. This applies regardless of the breadth of the range.

The practice of the present invention may employ, unless otherwise indicated, conventional techniques of organic chemistry, polymer technology, molecular biology (including recombinant techniques) cell biology, biochemistry, and immunology, which are within the skill of the art. Such conventional techniques include polymer array synthesis, hybridization, ligation, and detection of hybridization using a label. Specific illustrations of suitable techniques can be had by reference to the example hereinbelow. However, other equivalent conventional procedures can, of course, also be used. Such conventional techniques can be found in standard laboratory manuals such as *Genome Analysis: A Laboratory Manual Series (Vols. I–IV), Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), all of which are herein incorporated in their entirety by reference for all purposes.

Some aspects of the present invention make use of microarrays, also called arrays. Methods and techniques applicable to array synthesis have been described in U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, and 6,090,555. All of the above patents incorporated herein by reference in their entireties for all purposes.

(B) Definitions

Nucleic acids according to the present invention may include any polymer or oligomer of pyriridine and purine bases, preferably cytosine, thymine, and uracil, and adenine and guanine, respectively. (See Albert L. Lehninger, PRINCIPLES OF BIOCHEMISTRY, at 793–800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof, which may be isolated from natural sources, recombinantly produced or artificially synthesized. (See U.S. Pat. No. 6,156,501 which is hereby incorporated by reference in its entirety.) A further example of a polynucleotide of the present invention may be a peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "fragment," "segment," or "DNA segment" refers to a portion of a larger DNA polynucleotide or DNA. A polynucleotide, for example, can be broken up, or fragmented into, a plurality of segments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," 3$^{rd}$ Ed. Cold Spring Harbor Laboratory Press, Cold Spring Harbor, N.Y. (2001) ("Sambrook et al.) [Table 12–1 on page 12.11] which is incorporated herein by reference for all purposes. These methods can be optimized to digest a nucleic acid into fragments of a selected size range. Useful size ranges may be from 100, 400, 700 to 1000, 1500, 2000 or 4000 bases, but larger size ranges such as 4000–10,000, 10,000–20,000 may also be useful.

"Genome" designates or denotes the complete, single-copy set of genetic instructions for an organism as coded into the DNA of the organism. A genome may be multi-chromosomal such that the DNA is cellularly distributed among a plurality of individual chromosomes. For example, in human there are 22 pairs of chromosomes plus a gender associated XX or XY pair.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3\times10^9$ bp. The largest chromosome, chromosome no. 1, contains about $2.4\times10^8$ bp while the smallest chromosome, chromosome no. 22, contains about $5.3\times10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

The term "target sequence", "target nucleic acid" or "target" refers to a nucleic acid of interest. Selection probes are designed to hybridize to a target sequence. The term target nucleic acid may refer to the specific subsequence of a larger nucleic acid to which the probe is directed or to the overall sequence. The target sequence may or may not be of biological significance. Typically, though not always, it is the significance of the target sequence, which is being studied, in a particular experiment. As non-limiting examples, target sequences may include regions of genomic DNA which are believed to contain one or more polymorphic sites, DNA encoding or believed to encode genes or portions of genes of known or unknown function, DNA encoding or believed to encode proteins or portions of proteins of known or unknown function, DNA encoding or believed to encode regulatory regions such as promoter sequences, splicing signals, polyadenylation signals, etc. The number of target sequences to be interrogated can vary but may be in the range of 1 to 1000, or 100 to 10,000 or 10,000 to 100,000 target sequences or up to 1,000,000 target sequences.

As used herein a "probe" or "selection probe" is defined as a nucleic acid, such as an oligonucleotide, capable of binding to a target nucleic acid of complementary sequence through one or more types of chemical bonds, usually through complementary base pairing, usually through hydrogen bond formation. As used herein, a probe may include natural or modified bases. A selection probe can be RNA or DNA. In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

A reference sample or reference population is a nucleic acid sample that comprises reference sequences. The reference sequences may be used as selection probes or they may be used as templates to prepare selection probes. Each reference sequence comprises a target sequence and may also comprise sequences useful for the methods of the current invention such as one or more primer binding sequences and one or more promoter sequences. The promoter may be, for example, a promoter for a RNA polymerase such as T7, SP6, or T3 RNA polymerase. Each of these polymerases is a DNA-dependent RNA polymerase that exhibits extremely high specificity for its cognate promoter sequence as a start site for transcription. DNA cloned downstream from a T3, T7 or SP6 promoter serves as a template for RNA synthesis. Methods and materials for in vitro transcription are well known in the art. See Sambrook et al. (2001), New England BioLabs Catalog, and Promega Catalog all of which are herein incorporated in their entirety by reference for all purposes. The reference sample may further comprise a collection of cloning vectors with inserts wherein each insert may comprise a reference sequence. The reference sample can be used to generate a collection of selection probes.

A "cloning vector" is typically a DNA molecule originating from a virus, a plasmid, or the cell of a higher organism into which another DNA fragment of appropriate size can be integrated without loss of the vector's capacity for self replication. Vectors are often used to introduce foreign DNA into host cells where the DNA can be reproduced in large quantities. Examples are plasmids, cosmids, yeast artificial chromosomes (YACs) and bacteria artificial chromosomes (BACs). Vectors may be recombinant molecules containing DNA sequences from several sources.

An "array" comprises a support, preferable solid, with nucleic acid probes attached to said support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744, 305, 5,677,195, 5,800,992, 6,040,193, 5,424,186 and Fodor et al., Science, 251:767–777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. No. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.)

Arrays may be packaged in such a manner as to allow for diagnostic use or can be an all-inclusive device; e.g., U.S. Pat. Nos. 5,856,174 and 5,922,591 incorporated in their entirety by reference for all purposes.

Preferred arrays are commercially available from Affymetrix and are directed to a variety of purposes, including genotyping and gene expression monitoring for a variety of eukaryotic and prokaryotic species. (See Affymetrix Inc., Santa Clara and their website at affymetrix.com.) A "polymorphism" is an allelic variation between two nucleic acids. Polymorphisms include differences in nucleotide sequence, mutations, insertions, deletions, point mutations as well as strand breaks or chemical modifications. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

Single nucleotide polymorphisms (SNPs) are positions at which two alternative bases occur at appreciable frequency (>1%) in the human population, and are the most common type of human genetic variation.

"Adaptor sequences" or "adaptors" are generally oligonucleotides of at least 5 or 10 bases and preferably no more than 50 or 60 bases in length, however, they may be even longer, up to 100 or 200 bases. Adaptor sequences may be synthesized using any methods known to those of skill in the art. For the purposes of this invention they may, as options, comprise templates for PCR primers, restriction sites and promoters. The adaptor may be entirely or substantially double stranded. The adaptor may be phosphorylated or unphosphorylated on one or both strands. Adaptors are particularly useful in one embodiment of the current invention if they comprise a substantially double stranded region and short single stranded regions which are complementary to the single stranded region created by digestion with a restriction enzyme. For example, when DNA is digested with the restriction enzyme EcoRI the resulting double stranded fragments are flanked at either end by the single stranded overhang 5'-AATT-3', an adaptor that carries a single stranded overhang 5'-TTAA-3' will hybridize to the fragment through complementarity between the overhanging regions. This "sticky end" hybridization of the adaptor to the fragment may facilitate ligation of the adaptor to the fragment but blunt ended ligation is also possible. Methods of ligation will be known to those of skill in the art and are described, for example in Sambrook et at. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; *E. coli* DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'→5' phosphodiester bond, substrates include single-stranded RNA and DNA as well as dinucleoside pyrophosphates; or any other methods described in the art.

(C) The Process

In general, the currently claimed invention is to enable a user to reduce the complexity of a nucleic acid sample in a reproducible manner by enriching specific nucleic acid target sequences in the population. The resulting enriched sample is particularly suitable for a variety of biological analyses, such as genotyping, although one of skill in the art will recognize that other uses may be made of the enriched sample. In one embodiment the initial sample is enriched by hybridizing the sample to selection probes that are complementary to one or more sequences of interest and the resulting probe-target complexes are selectively amplified.

In one embodiment the currently claimed invention provides a method of enriching for specific nucleic acid target sequences in a sample nucleic acid population. In this embodiment, the currently claimed invention provides a method of amplifying a population of target sequences wherein each of said target sequences comprises a region of interest. The method comprises fragmenting the nucleic acid population, ligating an adaptor sequence to the 5' end of the fragments, leaving a free 3' OH, and exposing the fragments to selection probes. The selection probes comprise a region that is complementary to the target sequence and carries a unique sequence at the 5'. The unique sequence at the 5' end is common to all of the selection probes in the pool. Complementary target sequences and selection probes are allowed to hybridize, forming probe-target complexes. The 3' end of the target sequence should hybridize within the selection probe. The target is then extended at the 3' end using the unique sequence from the 5' end of the selection probe as a template. The extended target can then be selectively amplified using primers that recognizes the unique sequence added by extension and a second primer that recognizes the 5' adaptor sequence in the target. As an option, these target sequences may be analyzed using any variety of methods.

FIG. 1 depicts a schematic illustration of the general steps of a preferred embodiment of the currently claimed invention. The selection probes may be produced in a variety of ways, for example, they can be created by enriching a DNA sample for regions of interest and modifying the fragments by the ligation of adaptors at both ends to make a reference sample. In the embodiment illustrated in FIG. 1 the adaptors contain a promoter region for an RNA polymerase P1 and a unique sequence P2 that can serve as a primer binding site and template for extension of the target, while the second adaptor contains a sequence P3 that can also serve as a unique primer binding site. RNA that is complementary to the target sequence and has primer binding sites P2 and P3 is then transcribed from the reference sample. A sample nucleic acid population is fragmented by, for example, restriction enzyme digestion, and an adaptor with a third unique sequence P4 is ligated to the fragments so that the ligation occurs only at the 5' end of the fragments. The fragments are mixed with the RNA selection probes under conditions that allow hybridization of the RNA selection probes and the complementary target sequences. The target sequence is then extended using the RNA selection probe as template so that the complement of unique sequence P2 will be incorporated into the 3' end of the target. The target can then be amplified by PCR using primers that recognize P2 and P4. The selection probes are not amplified because they lack a primer binding site.

Methods of RNA dependent DNA synthesis are well known to those of skill in the art. (See, e.g. Sambrook et al.) In a preferred embodiment, the selection probes are RNA, the target molecules are DNA and the target molecule is extended in the presence of reverse transcriptase and dNTPs. Reverse transcriptase may be any enzyme that is capable of synthesizing a corresponding cDNA from an RNA template in the presence of the appropriate primers and nucleoside triphosphates. In a preferred embodiment, the reverse transcriptase may be from avian myeloblastosis virus (AMV), Moloney murine leukemia virus (MMULV) or Rous Sarcoma Virus (RSV), for example, and may be thermal stable (e.g. rTth DNA polymerase available from PE Applied Biosystems, Foster City, Calif.).

In one embodiment, the adaptor ligation is blocked at the 3' end of the target nucleic acid. The adapter can be designed so that the 5' end of the target strand can be covalently joined to the adaptor, but the end 3' end cannot. Any known method to block ligation at the 3' end of the target strand may be employed. For example, one strand of the adaptor can be designed to introduce a gap of one or more nucleotides between the 5' end of that strand of the adaptor and the 3' end of the target nucleic acid. Adapters can be designed specifically to be ligated to the termini produced by restriction enzymes and to introduce gaps or nicks. For example, if the target is an EcoRI digested fragment an adapter with a 5' overhang of TTA could be ligated to the AATT overhang left by EcoRI to introduce a single nucleotide gap between the adaptor and the 3' end of the fragment. Phosphorylation and kinasing can also be used to selectively block ligation of the adaptor to the 3' end of the target molecule. Absence of a phosphate from the 5' end of an adaptor will block ligation of that 5' end to an available 3'OH. Blocked phosphorylation can be used to introduce a gap where the fragments have blunt ends. For additional adaptor methods for selectively blocking ligation see U.S. Pat. No. 6,197,557 which is incorporated by reference herein in its entirety for all purposes.

Figure 2:
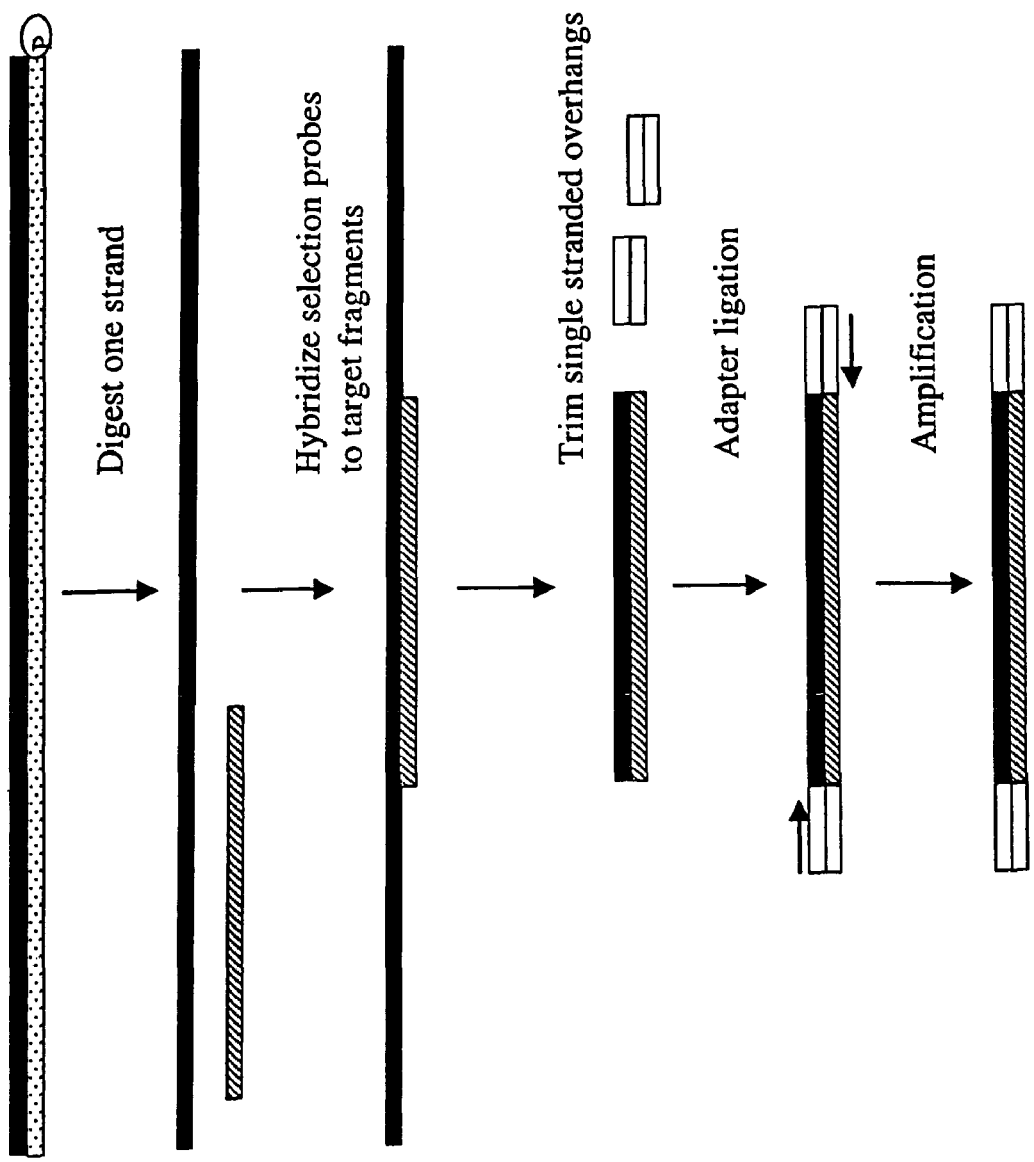
FIG. 2 is a schematic illustration of a method for amplifying a target sequence from a nucleic acid population by hybridizing selection probes to target molecules and digesting non-hybridized nucleic acid.

In another embodiment, schematically illustrated in FIG. 2, the presently claimed invention provides a method comprising: fragmenting a double stranded population, making the population single stranded by selectively degrading one strand, exposing the fragments to selection probes to form target-probe complexes, removing single stranded nucleic acids, leaving completely double stranded probe-target complexes, ligating adaptors to the ends of the probe-target complexes and amplifying the probe target complexes using primers that are complementary to the adaptors. The selection probes comprise a region that is complementary to the region of interest.

Sample Nucleic Acid

The single-stranded or double-stranded nucleic acid populations according to the present invention may refer to any mixture of two or more distinct species of single-stranded mRNA, DNA or double-stranded DNA, which may include DNA representing genomic DNA, genes, gene fragments, oligonucleotides, polynucleotides, nucleic acids, PCR products, expressed sequence tags (ESTs), or nucleotide sequences corresponding to known or suspected single nucleotide polymorphisms (SNPs), having nucleotide sequences that may overlap in part or not at all when compared to one another. The species may be distinct based on any chemical or biological differences, including differences in base composition, order, length, or conformation. The single-stranded DNA population may be isolated or produced according to methods known in the art, and may include single-stranded cDNA produced from a mRNA template, single-stranded DNA isolated from double-stranded DNA, or single-stranded DNA synthesized as an oligonucleotide. The double-stranded DNA population may also be isolated according to methods known in the art, such as PCR, reverse transcription, and the like. It may be obtained from any biological or environmental source, including plant, animal (including human), bacteria, fungi or algae. Any suitable biological sample can be used for assay of genomic DNA. Convenient suitable samples include whole blood, tissue, semen, saliva, tears, urine, fecal material, sweat, buccal, skin and hair.

The region of interest may be of any length and may comprise any sequence. For example, the region of interest may be a polymorphic site and comprise a single nucleotide base or may be an entire chromosome and comprise a million or more nucleotide bases. The region of interest may contain a variable region. The variable region may or may not be associated with a particular phenotype.

Those of skill in the art will be familiar with the digestion of nucleic acids with restriction enzymes. In a preferred embodiment of the invention, particularly when genomic DNA is used as the sample source, a combination of restriction enzymes is used, as specific combinations of restriction enzymes may result in a larger percentage of genomic DNA fragments of suitable length for amplification. As one of skill in the art will appreciate, longer DNA fragments are more difficult to amplify with high fidelity.

A specific restriction enzyme will typically cut the DNA at a given recognition sequence, and that recognition sequence statistically appears in the genomic DNA every X number of base pairs, where X varies with the length of the given recognition sequence (i.e. restrictions enzymes which have four base recognition site will cut more frequently than restriction enzymes with a six or eight base recognition site).

Thus, the combination of restriction enzymes to be used may be altered to produce fragments in a desired range of sizes. One of skill in the art will appreciate that there are many different restriction enzymes available and many different recognition sequences. See New England BioLabs Catalog, available at www.neb.com, which is herein incorporated by reference in its entirety for all purposes. In addition, some restriction enzymes, including but not limited to ApoI, AseI, BamHI, BssHII, EcoRI, EcoRV, HindIII, HinII, KpnI, PstI, PvuI, SalI, ScaI, TaqI and XmnI, are known to possess "star activity," meaning that under certain conditions, such as high glycerol concentrations, high amounts of restriction enzyme, low ionic strength, high pH, the presence or certain organic solvents, such as DMSO, recognize and cleave sequences not normally cleaved.

It may be desirable to use enzymes that produce fragments of a desired length containing a target sequence. Using publicly available databases of sequence, in silico digestion can be used to predict the size of a fragment containing a given target sequence when genomic DNA is digested with one or more restriction enzymes. For example, a computer program queries an electronic database containing the sequence of the DNA sample looking for sites which will be recognized by the enzyme being used. The method of modeling experiments can be employed for a wide variety of experiments. For example, if a user desires to isolate a particular sequence of interest in a fragment which has been digested with a restriction enzyme, the user can have the computer model the possible outcomes using a wide variety of restriction enzymes. The particular sequence which is selected may be chosen by specific criteria, i.e. because the region is believed to be associated with specific genes, polymorphisms, or phenotypes for example, or may be chosen at random. The user can then select the restriction enzyme which, for example, isolates the desired sequence in a fragment of a desired size. For example, if the target sequence is a SNP a computer can be used to analyze the sequence surrounding that SNP to identify restriction enzymes that cut downstream and upstream of the SNP to produce a fragment in the desired size range containing the SNP.

BglII, HindIII, XbaI and EcoRI are restriction enzymes that are particularly useful in the invention because many of the SNPs identified by The SNP Consortium (TSC) were identified from clones that were generated by digesting genomic DNA with these enzymes. See Altshuer et al. Nature, 407: 513–516 (2000) which is herein incorporated in its entirety by reference for all purposes. As a result many of these SNPs will be near a recognition sequence for at least one of these enzymes.

It may be desirable to denature the target sequence prior to exposure to the selection probes. Those of skill in the art will be familiar with many ways to denature nucleic acid, including heat, low salt, high pH, etc. See Sambrook et al. Denaturation may take place before or after fragmentation. Whether to denature before or after fragmentation may depend on the method of fragmentation employed. Furthermore, if adaptor sequences are to be attached, as described below, it may be preferable to attach double stranded adaptor sequences to double stranded fragments prior to denaturation. Alternatively some methods of adaptor attachment may require a single-stranded template.

Preparation of Selection Probes

The selection probes may be obtained from any number of sources. For example they may be RNA transcribed from a reference sample, PCR products amplified from a reference sample, fragments of a reference sample, DNA isolated from a gel fragment, PCR products generated from multiplex PCR or AP PCR, synthetic oligonucleotides, etc. For example, selection probes can be produced by fragmenting a nucleic acid population, ligating an adaptor comprising a phage promoter sequence and a primer binding site to one end of each fragment and a second adaptor comprising a primer binding site to the other end of each fragment. Fragments that comprise regions of interest can be selected and single stranded RNA can be transcribed from the selected fragments and used as selection probes. Alternatively the selected fragments can be cloned into a cloning vector to produce a library. In one embodiment the selection probes are preferably single stranded but may also be double stranded. In one embodiment, the selection probe will be complementary to the 3' end of the target molecule with a single stranded 5' overhang comprised of at least a primer binding site (see FIG. 1). A non-limiting example of a method to achieve this is to fragment the sample nucleic acid by the same method used to fragment the reference sample or prepare the selection probes. For example, if the reference sample was prepared by fragmenting genomic DNA with the restriction enzyme BglII and Sau3A then the sample nucleic acid could also be digested with BglII and Sau3A so that the target sequences will be contained on Bgm-sau3A fragments. The selection probe and target sequence should then share the same end point, a BglII or Sau3A restriction site. Alternatively any method of fragmentation that results in the 3' end of the target sequence hybridizing within the 5' end of the selection probe could be used.

The length of the selection probe may vary. The length need only be long enough to hybridize specifically to the desired region. The selection probe is preferably at least 20 or 30 bases but may be as many as 500, 1000 to 10,000 bases.

The complementary region of each selection probe may be different, or the selection probes may all include identical complementary regions. The complementary regions may comprise any sequence which will selectively hybridize to at least a portion of the region of interest. Thus, if the region of interest is very long, such as a partial chromosomal regions, the complementary region need not be exactly complementary to the chromosomal region, it need only be capable of selectively hybridizing to the chromosomal region with a higher affinity than any of the other sequences in the nucleic acid population. Preferably, the region is at least 50%, 80%, 85%, 90%, 95%, 97% or 99% complementary. The presently claimed invention does not require that each of the selection probes hybridize to a nucleic acid fragment. It is acceptable for only a small portion of the pool of selection probes to hybridize to nucleic acid fragments from a given sample. In this manner, generic selection probe pools may be created which can be used for a variety of different samples. Some selection probes may be capable of hybridizing to nucleic acid fragments from a number of different samples while others are sample specific. For example, a selection probe pool may contain probes with complementary regions for sequences which are known to be conserved between two or more different species. The same selection probe pool may also contain complementary regions for species-specific sequences. This same probe pool could then be used to enrich samples provided from one or more of the species. As an alternate example, a selection probe pool may contain probes with complementary regions for sequences known to carry a polymorphism. The selection probe pool may contain sequences complementary to more than one allele or for all known alleles. The same selection probe pool could be used to enrich samples provided from individuals carrying only one or two alleles.

Selection probes may be generated from a reference sample. The reference may represent a subset of a nucleic acid sample, for example a subset of a genome or a subset of the set of transcribed sequences from a genome. The subset may be separated from the first nucleic acid sample randomly, on the basis of specific sequence content or by a combination of the two approaches. One example of a random approach is to fragment the first nucleic acid sample, separate the fragments based on size and isolate fragments of a specific size range. Arbitrarily primed PCR (AP PCR) with random primers which have specific nucleotides incorporated into the primers is another method to obtain a reduced representation of a complex nucleic acid sample (See U.S. application Ser. No. 09/428,350 which is incorporated by reference in its entirety for all purposes). AP PCR is described in U.S. Pat. No. 5,487,985 which is incorporated by reference in its entirety for all purposes.

One example of a sequence specific method for generating a subset is to amplify target sequences from a first nucleic acid sample using PCR primers designed to amplify specific sequences of interest. Multiplex PCR in which many primer pairs are mixed in the same PCR reaction can be used (U.S. application Ser. No. 09/076,575 incorporated herein by reference for all purposes) or the PCR reactions can be done individually and the products pooled. Another method is to hybridize the reference sample to probes attached to a solid support, wash away unhybridized nucleic acids and elute the hybridized nucleic acids. The probes attached to the solid support can be designed to hybridize to a plurality of sequences of interest.

The reference sample may be designed to amplify a variety of target sequences. In one embodiment the target sequences comprise known SNPs. Those of skill in the art will appreciate that the subset may be generated in a variety of ways. For example, the subset may be generated by digesting genomic DNA with one or more restriction enzymes. Fragments of a certain size range, for example 100, 400, 500 or 700 base pairs, to 1000, 1500 or 2000 base pairs, can be isolated by running the digested DNA on a gel and cutting out the band corresponding to the desired size range. Other ways to randomly reduce the complexity of a sample include rapid PCR in which short extension and annealing times are used favoring amplification of only short fragments. Alternatively, a genomic DNA sample could be digested with two restriction enzymes followed by selective amplification of the subset of fragments cut by both restriction enzymes. U.S. application Ser. No. 09/428,350, which is herein incorporated by reference in its entirety for all purposes, describes additional methods for complexity reduction of complex samples of nucleic acids. Any other method that results in the preferential amplification of a subset of a nucleic acid sample could also be used.

In one preferred embodiment two or more restriction enzymes are used and in a particularly preferred embodiment the enzymes used may be chosen so that they cut leaving an enzyme specific overhang. Adaptors that are specific for the overhang of each restriction enzyme may be ligated to the fragments so that the adaptor ligated to one end of a fragment is different from the adaptor ligated to the other end of that fragment.

Templates for the selection probes can be generated by PCR using unique primer pairs to amplify regions of interest. In a preferred embodiment one of the primers comprises a phage promoter for in vitro transcription of RNA. Examples of phage promoters include the SP6, T7 and T3

RNA polymerase promoter sequences. Templates for selection probes may also be selected by hybridization to an array followed by washing to remove unhybridized nucleic acid and elution of the selected nucleic acid.

Hybridization and Analysis

Those of skill in the art will be familiar with conditions required to allow for suitable hybridization between the target sequence and the selection probe. See for example, Sambrook et al., "Molecular Cloning: A Laboratory Manual," $3^{nd}$ Ed. Cold Spring Harbor Laboratory Press, Cold Spring Harbor, N.Y. (2001) ("Sambrook et al.) which is incorporated herein by reference for all purposes.

In one embodiment of the present invention, prior to hybridization of the selection probes to the target sequences the double stranded target is made single stranded by, for example, selectively digesting one of the strands. Any known method of digestion may be employed. In a preferred embodiment Lambda exonuclease is used. Lambda exonuclease acts in the 5' to 3' direction, catalyzing the removal of 5' mononucleotides from duplex DNA. See, for example, New England Biolabs catalog or www.neb.com. The preferred substrate is 5'-phosphorylated double stranded DNA. In another preferred embodiment exonuclease III is used.

In the embodiment which uses an array, the nucleic acid sample is fragmented and the fragments are exposed to the nucleic acid array. Fragments which contain regions which are complementary to the immobilized probes will hybridize to the array. After hybridization, non-hybridized fragments are removed. The hybridized fragments are then eluted from the array producing a pool of fragments which is enriched for those sequences which are complementary to the immobilized selection probes. See, U.S. Pat. No. 6,013,440.

There are many known methods of amplifying nucleic acid sequences including e.g., PCR. See, e.g., *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., PCR Methods and Applications 1, 17 (1991); PCR (eds. McPherson et al., IRL Press, Oxford); and U.S. Pat. No. 4,683,202, which are incorporated by reference in their entireties for all purposes.

Other suitable amplification methods include the ligase chain reaction (LCR) (e.g., Wu and Wallace, *Genomics* 4, 560 (1989) and Landegren et al., *Science* 241, 1077 (1988)), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NABSA). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively.

As those of skill in the art will appreciate, after isolation and amplification, the resulting sequences may be further analyzed using any known method including sequencing, HPLC, hybridization analysis, cloning, labeling, etc.

In a preferred embodiment, isolated and amplified sequences are hybridized to probes which are immobilized to a solid support, such as a DNA microarray. The sequences prepared according to the methods of the presently claimed invention are appropriate for both directed arrays and generic "tag" arrays.

In directed arrays, the immobilized probes on the array comprise sequences which are designed to be complementary to the sequences being interrogated (interrogation sequence). Examples of commercially available directed arrays are the Gene Chip® HuSNP™ Probe Array and the Gene Chip® *Drosophila* Genome Array (both commercially available from Affymetrix, Inc., Santa Clara, Calif.). These arrays interrogate specific sequences from human and *Drosophila* respectively and enable the investigator to determine if the specific sequence is present in a given sample. See, U.S. Pat. Nos. 5,445,934, 5,744,305, 5,800,992, 5,837, 832, 5,861,242, 5,874,219, 6,027,880, 6,040,193, 6,156,501, International Patent applications PCT/US95/07377, PCT/US96/14839, and PCT/US96/14839 and Fodor et al., Science, 251:767–777 (1991), each of which is incorporated by reference in its entirety for all purposes.

In generic tag arrays, the immobilized probes are not designed to be complementary to a specific biological sequence to be interrogated. Rather, the probes are designed to be complementary to a set of unique tag sequences which can be attached to any sequence to be interrogated. The tag arrays allow for flexibility in the analysis to be performed. An example of a commercially available tag array is the Gene Chip® GenFlex array (Affymetrix, Inc., Santa Clara, Calif.) Sequences prepared using the methods described in the currently claimed invention may be particularly well suited for use with a generic tag array since the adaptor sequences used to amplify the target sequences may be designed to contain a tag sequence which will hybridize to a probe on the tag array. See, U.S. Pat. Nos. 5,800,992 and 6,013,445 and (EP pub for 2010).

The materials for use in the present invention are ideally suited for the preparation of a kit suitable for enriching specific nucleic acid target sequences. Such a kit may comprise various reagents utilized in the methods, preferably in concentrated form. The reagents of this kit may comprise but are not limited to a defined plurality of selection probes or a reference nucleic acid sample that can be used as template to synthesize a defined plurality of selection probes, buffer, appropriate nucleotide triphosphates, a reverse transcriptase, a nuclease, restriction enzymes, adaptors, a ligase, primers and instructions for the use of the kit.

METHODS OF USE

The methods of the presently claimed invention can be used for a wide variety of applications. Any analysis of genomic DNA may be benefited by a reproducible method of complexity management. Furthermore, the methods and enriched fragments of the presently claimed invention are particularly well suited for study and characterization of extremely large regions of genomic DNA.

In a preferred embodiment, the methods of the presently claimed invention are used for SNP discovery and to genotype individuals. For example, any of the procedures described above, alone or in combination, could be used to isolate the SNPs present in one or more specific regions of genomic DNA. Selection probes could be designed and manufactured to be used in combination with the methods of the invention to amplify only those fragments containing regions of interest, for example a region known to contain a SNP. Arrays could be designed and manufactured on a large scale basis to interrogate only those fragments containing the regions of interest. Thereafter, a sample from one or more individuals would be obtained and prepared using the same techniques which were used to prepare the selection probes or to design the array. Each sample can then be hybridized to an array and the hybridization pattern can be analyzed to determine the genotype of each individual or a population of individuals. Methods of use for polymorphisms and SNP discovery can be found in, for example, co-pending U.S. application Ser. Nos. 08/813,159 and 09/428,350 which are herein incorporated by reference in their entirety for all purposes).

Correlation of Polymorphisms with Phenotypic Traits

Most human sequence variation is attributable to or correlated with SNPs, with the rest attributable to insertions or deletions of one or more bases, repeat length polymorphisms and rearrangements. On average, SNPs occur every 1,000–2,000 bases when two human chromosomes are compared. (See, The International SNP Map Working Group, Science 409: 928–933 (2001) incorporated herein by reference in its entirety for all purposes.) Human diversity is limited not only by the number of SNPs occurring in the genome but further by the observation that specific combinations of alleles are found at closely linked sites.

Correlation of individual polymorphisms or groups of polymorphisms with phenotypic characteristics is a valuable tool in the effort to identify DNA variation that contributes to population variation in phenotypic traits. Phenotypic traits include physical characteristics, risk for disease, and response to the environment. Polymorphisms that correlate with disease are particularly interesting because they represent mechanisms to accurately diagnose disease and targets for drug treatment. Hundreds of human diseases have already been correlated with individual polymorphisms but there are many more diseases that are known to have an, as yet unidentified, genetic component and many diseases for which a component is or may be genetic.

Many diseases may correlate with multiple genetic changes making identification of the polymorphisms associated with a given disease more difficult. One approach to overcome this difficulty is to systematically explore the limited set of common gene variants for association with disease.

To identify correlation between one or more alleles and one or more phenotypic traits, individuals are tested for the presence or absence of polymorphic markers or marker sets and for the phenotypic trait or traits of interest. The presence or absence of a set of polymorphisms is compared for individuals who exhibit a particular trait and individuals who exhibit lack of the particular trait to determine if the presence or absence of a particular allele is associated with the trait of interest. For example, it might be found that the presence of allele A1 at polymorphism A correlates with heart disease. As an example of a correlation between a phenotypic trait and more than one polymorphism, it might be found that allele A1 at polymorphism A and allele B1 at polymorphism B correlate with a phenotypic trait of interest.

Diagnosis of Disease and Predisposition to Disease

Markers or groups of markers that correlate with the symptoms or occurrence of disease can be used to diagnose disease or predisposition to disease without regard to phenotypic manifestation. To diagnose disease or predisposition to disease, individuals are tested for the presence or absence of polymorphic markers or marker sets that correlate with one or more diseases. If, for example, the presence of allele A1 at polymorphism A correlates with coronary artery disease then individuals with allele A1 at polymorphism A may be at an increased risk for the condition.

Individuals can be tested before symptoms of the disease develop. Infants, for example, can be tested for genetic diseases such as phenylketonuria at birth. Individuals of any age could be tested to determine risk profiles for the occurrence of future disease. Often early diagnosis can lead to more effective treatment and prevention of disease through dietary, behavior or pharmaceutical interventions. Individuals can also be tested to determine carrier status for genetic disorders. Potential parents can use this information to make family planning decisions.

Individuals who develop symptoms of disease that are consistent with more than one diagnosis can be tested to make a more accurate diagnosis. If, for example, symptom S is consistent with diseases X, Y or Z but allele A1 at polymorphism A correlates with disease X but not with diseases Y or Z. An individual with symptom S is tested for the presence or absence of allele A1 at polymorphism A. Presence of allele A1 at polymorphism A is consistent with a diagnosis of disease X. Genetic expression information discovered through the use of arrays has been used to determine the specific type of cancer a particular patient has. (See, Golub et al. Science 286: 531–537 (2001) hereby incorporated by reference in its entirety for all purposes.)

Pharmacogenomics

Pharmacogenomics refers to the study of how your genes affect your response to drugs. There is great heterogeneity in the way individuals respond to medications, in terms of both host toxicity and treatment efficacy. There are many causes of this variability, including: severity of the disease being treated; drug interactions; and the individuals age and nutritional status. Despite the importance of these clinical variables, inherited differences in the form of genetic polymorphisms can have an even greater influence on the efficacy and toxicity of medications. Genetic polymorphisms in drug-metabolizing enzymes, transporters, receptors, and other drug targets have been linked to interindividual differences in the efficacy and toxicity of many medications. (See, Evans and Relling, Science 286: 487–491 (1999) which is herein incorporated by reference for all purposes).

An individual patient has an inherited ability to metabolize, eliminate and respond to specific drugs. Correlation of polymorphisms with pharmacogenomic traits identifies those polymorphisms that impact drug toxicity and treatment efficacy. This information can be used by doctors to determine what course of medicine is best for a particular patient and by pharmaceutical companies to develop new drugs that target a particular disease or particular individuals within the population, while decreasing the likelihood of adverse affects. Drugs can be targeted to groups of individuals who carry a specific allele or group of alleles. For example, individuals who carry allele A1 at polymorphism A may respond best to medication X while individuals who carry allele A2 respond best to medication Y. A trait may be the result of a single polymorphism but will often be determined by the interplay of several genes.

In addition some drugs that are highly effective for a large percentage of the population, prove dangerous or even lethal for a very small percentage of the population. These drugs typically are not available to anyone. Pharmacogenomics can be used to correlate a specific genotype with an adverse drug response. If pharmaceutical companies and physicians can accurately identify those patients who would suffer adverse responses to a particular drug, the drug can be made available on a limited basis to those who would benefit from the drug.

Similarly, some medications may be highly effective for only a very small percentage of the population while proving only slightly effective or even ineffective to a large percentage of patients. Pharmacogenomics allows pharamaceutical companies to predict which patients would be the ideal candidate for a particular drug, thereby dramatically reducing failure rates and providing greater incentive to companies to continue to conduct research into those drugs.

Determination of Relatedness

There are many circumstances where relatedness between individuals is the subject of genotype analysis and the present invention can be applied to these procedures. Paternity testing is commonly used to establish a biological relationship between a child and the putative father of that child. Genetic material from the child can be analyzed for occurrence of polymorphisms and compared to a similar analysis of the putative father's genetic material. Determination of relatedness is not limited to the relationship between father and child but can also be done to determine the relatedness between mother and child, (see e.g. Staub et al., U.S. Pat. No. 6,187,540) or more broadly, to determine how related one individual is to another, for example, between races or species or between individuals from geographically separated populations, (see for example H. Kaessmann, et al. Nature Genet. 22, 78 (1999)).

Forensics

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance. A similar comparison of markers can be used to identify an individual's remains. For example the U.S. armed forces collect and archive a tissue sample for each service member. If unidentified human remains are suspected to be those of an individual a sample from the remains can be analyzed for markers and compared to the markers present in the tissue sample initially collected from that individual.

Marker Assisted Breeding

Genetic markers can assist breeders in the understanding, selecting and managing of the genetic complexity of animals and plants. Agriculture industry, for example, has a great deal of incentive to try to produce crops with desirable traits (high yield, disease resistance, taste, smell, color, texture, etc.) as consumer demand increases and expectations change. However, many traits, even when the molecular mechanisms are known, are too difficult or costly to monitor during production. Readily detectable polymorphisms which are in close physical proximity to the desired genes can be used as a proxy to determine whether the desired trait is present or not in a particular organism. This provides for an efficient screening tool which can accelerate the selective breeding process.

EXAMPLES

Example One

Figure 3A:
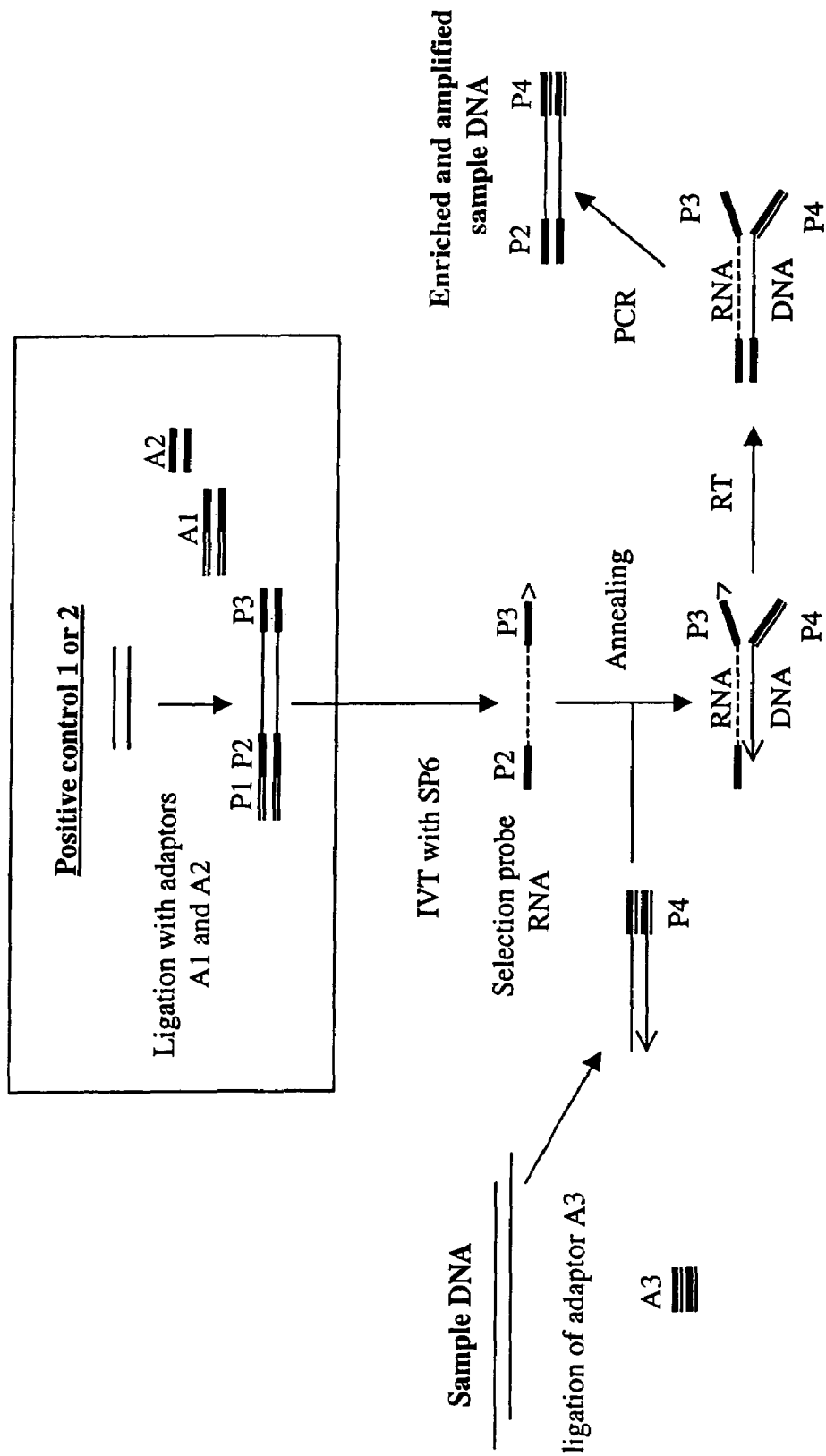
FIG. 3A is a schematic of an experiment amplifying targets from a complex mixture using selection probes transcribed from PCR products.

Amplifying known targets from a complex mixture using known PCR products to generate selection probes. (See FIG. 3A for a schematic and Table 1 for the sequences of the adaptors and primers used).

Step 1. Preparing sample DNA. Positive control DNA targets were mixed with background DNA to produce a complex sample mixture. To generate a first positive control, positive control 1, 88 different primers pairs were used to amplify 88 unique PCR products which were pooled in equimolar amounts. To generate a second positive control, positive control 2, 98 different primers pairs were used to amplify 98 unique PCR products which were pooled in equimolar amounts. The fragments were kinased and ligated to adapter, A3. Prior to ligation A3 was dephosphorylated to block ligation of the adaptor to the 3' end of each DNA.

The background DNA was isolated from human cell line K562 (Gibco BRL, Rockville, Md.) and digested with restriction enzymes MnlI and MseI (NEB, Beverly, Mass.) to an average size of 200 base pairs. The sample DNA was a mixture of both positive control DNAs, 1 and 2, and background DNA so that the ratio of a given positive control DNA fragment to the corresponding DNA fragment in the background DNA was either 20:1 or 1:1. (See, FIG. 3B.). The sample DNA was blunted with Klenow (NEB) before ligation to adaptors.

Step 2: Preparing selection probe RNA. To make the selection probes a sample of each positive control DNA, 1 or 2, was ligated to adaptors, A1 and A2 by blunt end ligation. Adaptor A1 contains an SP6 promoter sequence at its 5' end and part of the sequence of primer P2 at its 3' end. Adaptor A2 comprises the sequence of primer P3. The gaps after ligation were filled in by Klenow reaction and DNA fragments were amplified by PCR using P1P2 and P3. The fragments were used as templates for in vitro transcription using SP6 RNA polymerase to produce selection probes: RNA with the sequence of P2 at the 5' end and P3 at the 3' end Step 3: Hybridization and extension. The target fragments in the sample DNA were then hybridized to the selection probes and extended by reverse transcription as follows: 4 ul of each sample DNA, ~100 ng DNA, was mixed with 2 μl of selection probe RNA(~1×10$^{10}$ copies), 6 μl of 3.3×rTth polymerase buffer, 2 μl 2 mM dNTPs and 4 μl water. This mixture was heated to 95° C. for 1 min then cooled to 72° C. Then MnCl$_2$ was added to a final concentration of 2 mM and 0.4 units rTth DNA polymerase (Perkin Elmer, Foster City, Calif.) was added bringing the total volume to 201 μl. The reaction was incubated at 72° C. for 60 min.

Step 4: Amplification of target DNAs. To amplify only the positive control DNAs that were extended in the reverse transcription reaction, PCR was done using primers P2 and P4. The reaction contained 1× buffer II, 2 mM MgCl2, 0.2 mM dNTP, 0.4 μM P2 primer, 0.4 μM P4 primer, 0.5 μl (2.5 Units) TaqGold polymerase (Perkin Elmer, Foster City, Calif.) and 2 μl of the reverse transcription reaction. The program was 95° C. for 2 min and 45 cycles of 95° C. for 20 sec, 58° C. for 20 sec and 72° C. for 20 sec.

Standard procedures for labeling and hybridization of the sample to an array were used. The array interrogates approximately 13,000 selected SNPs. The PCR products were purified with QIAquick PCR Purification kit (Qiagen) according to the manufacturer's instructions and fragmented with DNase I.

The fragments were then labeled with biotin-N-6-ddATP as follows: In each tube, incubate 10 ug DNA with 0.3 unit DnaseI (Promega) at 37° C. for 30 minutes in a 45 μl mixture also containing 10 mM Tris-Actate (pH 7.5), 10 mM magnesium acetate and 50 mM potassium acetate. Stop the reaction by heating the sample to 95° C. for 15 minutes. Label the sample by adding 60 unit terminal transferase and 4 pmol biotin-N-6-ddATP (Dupont NEN) followed by incubation at 37° C. for 90 minutes and a final heat inactivation at 95° C. for 15 minutes.

The labeled DNA was then hybridized to an array in a hybridization mixture containing 80 ug labeled DNA, 160 ug human COT-1 DNA (GIBCO), 3.5 M tetramethylamonium cloride, 10 mM MES. (pH 6.5), 0.01% Triton-100, 20 ug herring sperm DNA, 100 ug bovine serum albumin and 200 pM control oligomer at 44° C. for 40 hours on a rotisserie at 40 rpm. The arrays were then washed with 0.1 M NaCl in 10 mM MES at 44° C. for 30 minutes on a rotisserie at 40 rpm. The hybridized arrays were then stained with a staining solution [10 mM MES (ph 6.5), 1 M NaCl, 10 ug/ml steptaviden R-phycoerythrin, 0.5 mg/ml acetylated BSA, 0.01% Triton-100] at 40° C. for 15 minutes. The arrays were then washed with 6×SSPET [0.9 M NaCl, 60 mM NaH2PO4 (pH 7.4), 6 mM EDTA, 0.005% Triton-100] on a GeneChip® Fluidics Station (Affymetrix, Inc., Santa Clara, Calif.) 10 times at 22° C. The arrays were then anti-streptavidin antibody stained at 40° C. for 30 minutes with antibody solution [10 mM MES (pH 6.5), 1 M NaCl, 10 ug/ml streptavidin R-phycoerythrin, 0.5 mg/ml acetylated BSA, 0.01% Triton-100]. The arrays are then restained with staining solution for 15 minutes followed by 6×SSPET washing as above. The arrays were then scanned with a confocal scanner at 560 nm. The hybridization patterns were then analyzed with a computer program.

As expected, when the selection probes used were RNA corresponding to positive control 1, hybridization was detected for the positive control 1 DNAs but not for the positive control 2 DNAs. Likewise, when the selection probes used were the RNA corresponding to positive control 2, hybridization was detected for the positive control 2 DNAs but not for the positive control 1 DNAs.

Example 2

Figure 4:
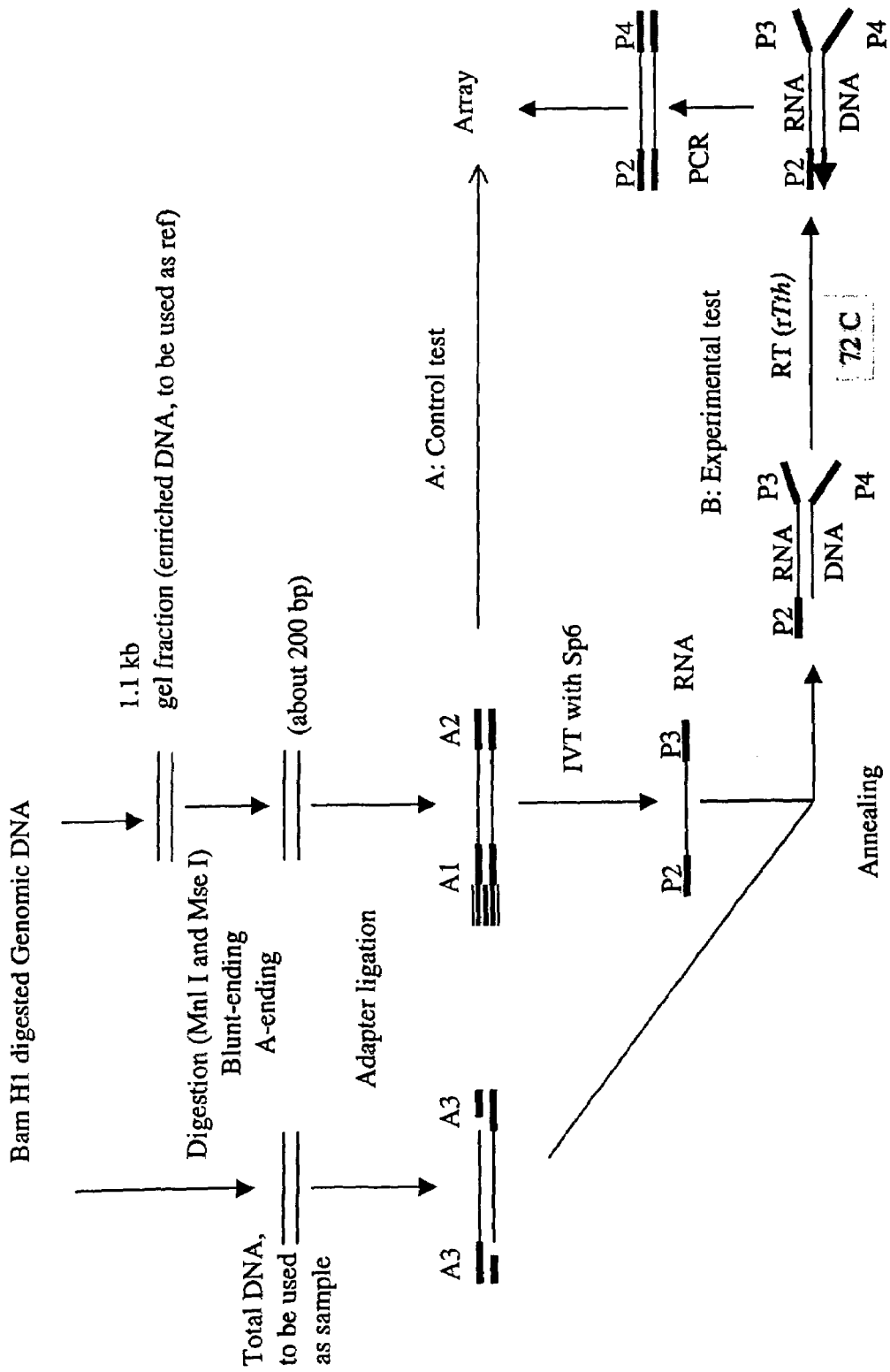
FIG. 4 is a schematic of an experiment amplifying targets from a genomic DNA sample using selection probes transcribed from fragments generated from a size selected gel fragment from a digest of genomic DNA.

Complexity reduction of genomic DNA using selection probes derived from a sub fraction of genomic DNA isolated from a gel. (See, FIG. 4)

Step 1: Sample DNA was genomic DNA digested to an average size of 100–200 base pairs using restriction enzymes BamHI, MnlI and MseI (NEB). After being blunt-ended by Klenow reaction, the DNA was ligated to un-phosphorylated adaptor A3 as in previous example (only the 5' phosphorylated genomic DNA fragment can be ligated at its 5' end with an adaptor strand, but not the 3' end).

Step 2: Preparation of selection probe RNA. Selection probes were prepared by digesting genomic DNA with BamHI, separating the fragments on a 0.8% agarose gel, cutting a band out of the gel corresponding to fragments of 1–1.2 kb and isolating the fragments from the gel slice. The isolated DNA was further digested to an average size of 100–200 base pairs using restriction enzymes MnlI and MseI. The fragments were blunted and adaptors, A1 and A2, were ligated to the fragments. RNA was transcribed from the fragments using SP6, as above.

Step 3: The selection probe RNA was hybridized to the sample DNA and extended using reverse transcription as above. The extended target DNA was then amplified using PCR and primers P2 and P4.

Step 4: Hybridization to an array and analysis.

The amplified target molecules were hybridized to an array as in Example one above. As a control, a sample of the template used for making the selection probe RNA was also hybridized to an array. The subset of fragments that are predicted to be found in the selection probes and to hybridize to the array were analyzed to determine the specificity of hybridization observed. Hybridization of the experimental sample was greater than the hybridization of the control sample.

TABLE 1

| SEQ ID NO: | Name | Description | Sequence |
|---|---|---|---|
| 1 | Adaptor A1 | Top strand | 5' GAATTGAATTTAGGTGACACTATAGAAGAGCG ACTCACTATAGGGAGA 3' |
| 2 | | Bottom strand | 3' TATGCTGAGTGATATCCCTCT 5' |
| 3 | Adaptor A2 | Top strand | 5' CGTTGTAAAACGACGGCCAGT 3' |
| 4 | | Bottom strand | 3' AACATTTTGCTGCCGGTCA 5' |
| 5 | Adaptor A3 | Top strand | 5' AGCGGATAACAATTTCACACA 3' |
| 6 | | Bottom strand | 3' CGCCTATTGTTAAAGTGTGT 5' |
| 7 | Primer P1P2 | | 5' GAATTGAATTTAGGTGACACTATAGAAGAGCG ACTCACTATAGGGAGA 3' |
| 8 | Primer P2 | | 5' GTGAATTGTAATACGACTCACTATAGGGAGA 3' |
| 9 | Primer P3 | | 5' CGTTGTAAAACGACGGCCAGT 3' |
| 10 | Primer P4 | | 5' AGCGGATAACAATTTCACACA 3' |

Example 3

Figure 5:
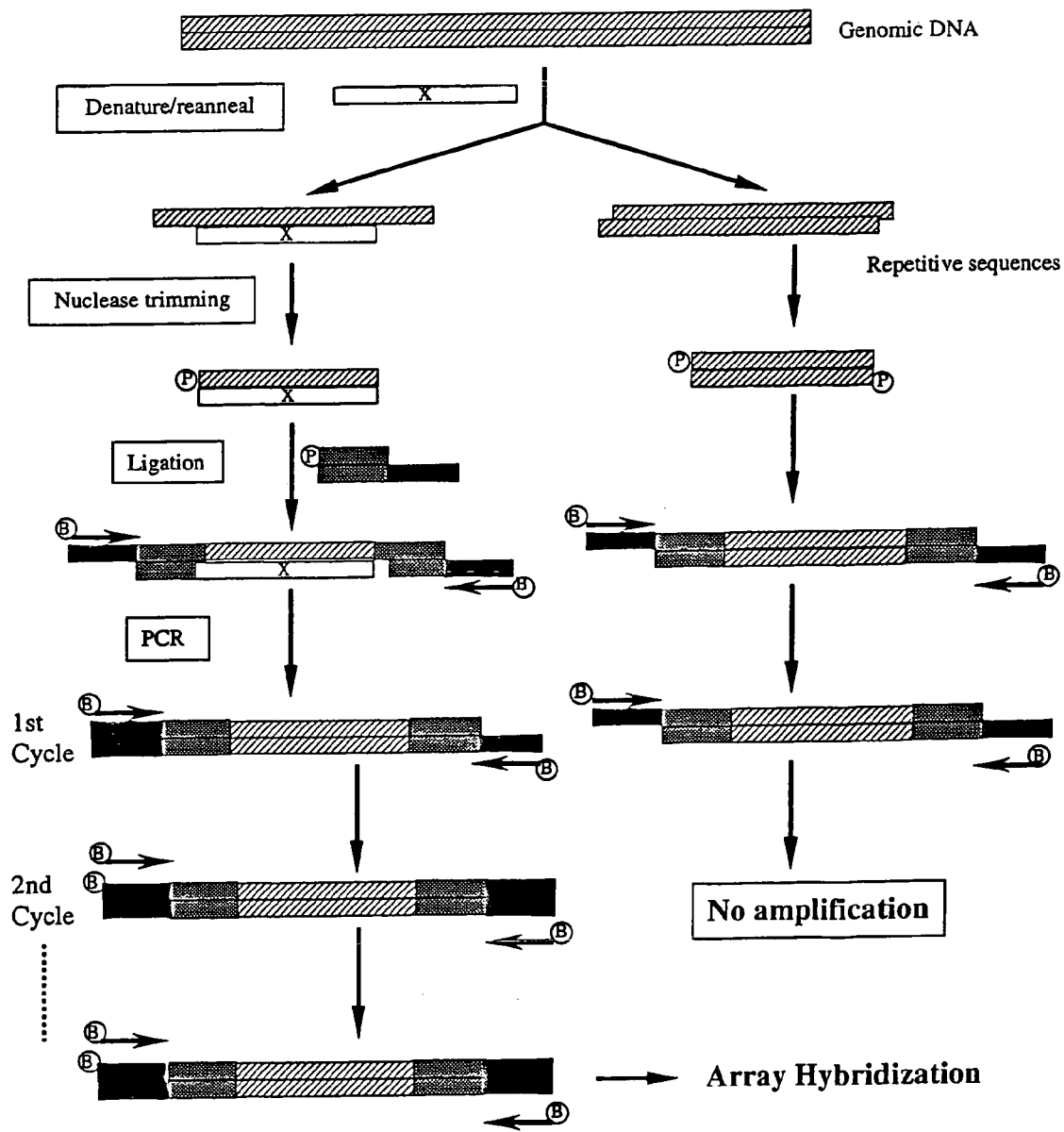
FIG. 5 is a schematic of an experiment amplifying targets from a genomic DNA sample using selection probes and nuclease trimming.

Complexity reduction by protection of targets by hybridized of selection probes. (See, FIG. 5).

Step 1. Fragment Target Genomic DNA

Digest 3 μg human genomic DNA with restriction enzymes Aat II (NEB), which generates 3' protruding ends, and Sau3A II (NEB) which generates 3'-recessed ends, in 50 μl 1×NEB buffer 4 at 37° C. overnight. Inactivate the enzymes at 65° C. for 20 minute.

Step 2. Generate Single Strand DNA by Exonuclease Digestion

Add to the above solution 1 unit exonuclease III (NEB) and incubate at 16° C. for 10 minutes. Heat inactivate the exonuclease and denature the DNA by incubation at 99° C., for 10 minutes. Cool on ice for 5 minute.

Step 3. Anneal Synthetic Selection Probes to Target DNA

Synthetic oligonucleotides are designed to be complementary to the strand that is not digested by the exonuclease. The oligonucleotides are mixed with the target genomic DNA in a 1000:1 ratio in NEB buffer4 (NEB) at 50° C. on a rotisserie for appropriate time.

Step 4. Trim off single strand DNA with nuclease

Add to the DNA solution 3 unit mung bean nuclease (NEB) and incubate at 30° C., for 30 minutes. Inactivate the nuclease by addition of SDS to 0.01%.

Step 5. Ligate Adaptors to DNA

Take one-tenth of the DNA solution in step 4 and ligate to adaptors (5'-ATTTAGGTGACACTATAGCCGGACT-GAATCATCAATGTAACA-3' (SEQ. ID NO: 11) and 5'-phophate-TGTTACATIGATCAITCAGTCCGdideoxyG-3'(SEQ. ID NO: 12)) in 1×T4 DNA ligase buffer (NEB) with 2000 unit T4 DNA ligase (NEB). Incubate at 16° C. for overnight. Inactivate the ligase by incubation at 65° C. for 10 minute.

Step 6. Amplify the Target with PCR

Amplify the target DNA (~$10^4$ copies for each target sequence in a 50 μl reaction) with 1 unit Taq polymerase and 0.5 mM primer (5'-biotin-ATTTAGGTGACACTATAG-3' (SEQ. ID NO: 13)) in 1×PCR buffer II (PE) with 2.5 mM $MgCl_2$. Incubate the PCR mixture at 72° C. for 10 minutes followed by 94° C. for 2 minutes and 35 cycles of 94° C. for 30 seconds, 48° C. for 30 seconds, 72° C. for 2 minutes.

CONCLUSION

From the foregoing it can be seen that the present invention provides a flexible and scalable method for analyzing complex samples of DNA, such as genomic DNA. These methods are not limited to any particular type of nucleic acid sample: plant, bacterial, animal (including human) total genome DNA, RNA, cDNA and the like may be analyzed using some or all of the methods disclosed in this invention. This invention provides a powerful tool for analysis of complex nucleic acid samples. From experiment design to isolation of desired fragments and hybridization to an appropriate array, the above invention provides for fast, efficient and inexpensive methods of complex nucleic acid analysis.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

We claim:

1. A method of genotyping an individual comprising:
    providing a first nucleic acid sample from said individual;
    obtaining a second nucleic acid sample by:
    fragmenting said first nucleic acid sample to form fragments;
    ligating an adaptor to one end of said fragments;
    exposing said fragments to a collection of selection probes, each of said selection probes comprising a single stranded region that is complementary to a region that is known or believed to contain a polymorphism and further comprising a unique sequence at the 5' end, under conditions to allow for hybridization between selection probes and target sequences to form a plurality of probe-target complexes;
    extending said target sequences in said probe-target complexes using the selection probe in the probe-target complex as template so that each target sequence will be extended at the 3' end to contain a sequence that is complementary to the unique sequence at the 5' end of the selection probe; and
    amplifying the extended target sequences using a first primer to said adaptor and a second primer to said unique sequence at the 5' end of the selection probe, thereby obtaining said second nucleic acid sample;
    providing a nucleic acid array wherein said array comprises probes designed to interrogate polymorphisms;
    hybridizing said second nucleic acid sample to said array;
    generating a hybridization pattern resulting from said hybridization; and
    determining the presence or absence of said polymorphism in the individual based upon an analysis of the hybridization pattern.

2. The method of claim 1 wherein said collection of selection probes is produced by fragmenting a reference population of nucleic acids to form fragments;
    ligating an adaptor to the ends of the fragments at least one of said adaptors comprising both a promoter for in vitro transcription and a primer binding site to obtain adaptor ligated fragments; and
    making cRNA from said adaptor ligated fragments.

3. The method of claim 2 wherein said cRNA is made using a RNA polymerase chosen from one or more of the following RNA polymerases: SP6, T3 and T7.

4. The method of claim 2 wherein said reference population is selected using a nucleic acid array.

5. The method of claim 2 wherein said reference population is selected using gel purification.

6. The method of claim 2 wherein said reference population is selected using a method to reduce the complexity of a genomic sample.

7. The method of claim 1 wherein said target sequence is extended by reverse transcriptase.

8. The method of claim 2 wherein said target sequence is extended by reverse transcriptase.

9. The method of claim 1 wherein said selection probes are complementary to one or more regions of said nucleic acid sample which are known or believed to be associated with a particular phenotype.

10. The method of claim 2 wherein said selection probes are complementary to regions of said nucleic acid sample which are known or believed to be associated with a particular phenotype.

11. The method of claim 2 wherein said reference population is fragmented using two or more restriction enzymes and said first nucleic acid sample is fragmented using at least one of the same restriction enzymes.

12. The method of claim 2 wherein said reference population is fragmented using at least two restriction enzymes and said first nucleic acid sample is fragmented using at least one of the same restriction enzymes.

13. The method of claim 2 wherein said reference population and said first nucleic acid sample are fragmented using the same method.

14. The method of claim 1 wherein said first nucleic acid sample is genomic DNA.

15. The method of claim 2 wherein said first nucleic acid sample is genomic DNA.

16. A method of genotyping an individual comprising:
providing a first nucleic acid sample from said individual;
obtaining a second nucleic acid sample by:
fragmenting said first nucleic acid sample to form fragments;
making said fragments single stranded;
exposing said fragments to a collection of selection probes, each of said selection probes comprising a single stranded region that is complementary to a region that is known or believed to contain a polymorphism, under conditions to allow for hybridization between selection probes and target sequences to form a plurality of probe-target complexes;
removing single stranded regions from the probe-target complexes to obtain completely double stranded probe-target complexes;
ligating adaptors to said double stranded probe-target complexes to obtain adaptor-ligated probe-target complexes; and
amplifying the adaptor-ligated probe target complexes thereby obtaining said second nucleic acid sample;
providing a nucleic acid array wherein said array comprises probes designed to interrogate polymorphisms;
hybridizing said second nucleic acid sample to said array;
generating a hybridization pattern resulting from said hybridization; and
determining the presence or absence of said polymorphism in the individual based upon an analysis of the hybridization pattern.

* * * * *

SEQUENCE LISTING

<160> NUMBER OF SEQ ID NOS: 13

<210> SEQ ID NO 1
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 1
gaattgaatt taggtgacac tatagaagag cgactcacta tagggaga        48

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
tctccctata gtgagtcgta t        21

<210> SEQ ID NO 3
<211> LENGTH: 21
<212> TYPE: DNA
<213> ORGANISM: Artificial Sequence
<220> FEATURE:

```
<223> OTHER INFORMATION: synthetic oligonucleotide

<400> SEQUENCE: 3
cgttgtaaaa cgacggccag t                                              21

<210> SEQ ID NO 4
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 4
actggccgtc gttttacaa                                                 19

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 5
agcggataac aatttcacac a                                              21

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
tgtgtgaaat tgttatccgc                                                20

<210> SEQ ID NO 7
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 7
gaattgaatt taggtgacac tatagaagag cgactcacta tagggaga                 48

<210> SEQ ID NO 8
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 8
gtgaattgta atacgactca ctatagggag a                                   31

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 9
cgttgtaaaa cgacggccag t                                              21
```

```
<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 10
agcggataac aatttcacac a                                             21

<210> SEQ ID NO 11
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 11
atttaggtga cactatagcc ggactgaatc atcaatgtaa ca                      42

<210> SEQ ID NO 12
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 12
tgttacattg atcattcagt ccgg                                          24

<210> SEQ ID NO 13
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 13
atttaggtga cactatag                                                 18
```